(12) United States Patent
Erben et al.

(10) Patent No.: US 8,820,672 B2
(45) Date of Patent: Sep. 2, 2014

(54) ENVIRONMENTAL SAMPLING WITH AN UNMANNED AERIAL VEHICLE

(75) Inventors: Erik Erben, Rio Rancho, NM (US);
Robert Habing, Albuquerque, NM (US);
Nader Tubbeh, Albuquerque, NM (US)

(73) Assignee: Honeywell International Inc., Morristown, NJ (US)

( * ) Notice: Subject to any disclaimer, the term of this patent is extended or adjusted under 35 U.S.C. 154(b) by 292 days.

(21) Appl. No.: 13/465,948

(22) Filed: May 7, 2012

(65) Prior Publication Data

US 2013/0292512 A1 Nov. 7, 2013

(51) Int. Cl.
*B64C 29/00* (2006.01)

(52) U.S. Cl.
USPC ........................................ 244/1 R; 244/23 C

(58) Field of Classification Search
USPC .................................. 244/1 R, 23 C
See application file for complete search history.

(56) References Cited

U.S. PATENT DOCUMENTS

| | | | |
|---|---|---|---|
| 6,442,997 | B1 | 9/2002 | Megerle et al. |
| 6,854,344 | B2 * | 2/2005 | Cornish et al. ............. 73/863.22 |
| 7,073,748 | B2 * | 7/2006 | Maurer et al. ................. 244/1 R |
| 7,096,749 | B2 * | 8/2006 | Schimmoller et al. ..... 73/863.21 |
| 7,841,563 | B2 * | 11/2010 | Goossen et al. ............. 244/175 |
| 7,998,731 | B2 * | 8/2011 | Daitch et al. ............... 435/309.1 |
| 2004/0185554 | A1 * | 9/2004 | Daitch et al. ............... 435/309.1 |
| 2009/0050750 | A1 * | 2/2009 | Goossen ..................... 244/76 R |
| 2011/0127421 | A1 | 6/2011 | Finlay |

FOREIGN PATENT DOCUMENTS

WO 2011103165 A1 8/2011

OTHER PUBLICATIONS

Gonzalez et al., "Development of an autonomous unmanned aerial system to collect time-stamped samples from the atmosphere and localize potential pathogen sources," Journal of Field Robotics 28(6): 961-976, Nov./ Dec. 2011 (First published online Oct. 12, 2011).
Griffin, "Atmospheric Sampling Using an Unmanned Aerial Vehicle (UAV)," found at http://uas.usgs.gov/pdf/ UAV_Equipment.pdf, accessed Feb. 8, 2008, 3 pp.
McHugh et al., "Update on an Unmanned Aerial Vehicle (UAV) Payload for Detection, Identification and Acquisition of Vapors of Toxic Substances and Their Precursors," 13th International Conference on Ion Mobility Spectrometry, 2004, 4 pp.
Ote Systems, Volcan UAV Project, Istituto Nazionale di Geofisica e Vulcanologia, Rome, Italy, downloaded Feb. 8, 2008, 7 pp.
Pöllänen et al., "Radiation surveillance using an unmanned aerial vehicle," Applied Radiation and Isotopes 67: 340-344, 2009.
Valyou et al., "Flight Control, Data Acquisition, and Payload Integration for an Aerosol Sampling Unmanned Aerial Vehicle," Department of Mechanical and Aeronautical Engineering, Clarkson University, Postdam, New York, 2007, 5 pp.

* cited by examiner

*Primary Examiner* — Tien Dinh
*Assistant Examiner* — Justin Benedik
(74) *Attorney, Agent, or Firm* — Shumaker & Sieffert, P.A.

(57) ABSTRACT

Environmental samples are collected and analyzed using an unmanned aerial vehicle (UAV). In some examples, the sample is drawn into engagement with a sensor onboard a UAV by the existing fluid flow generated by a rotor fan through a duct of a ducted fan of the UAV. The quality characteristics of the fluid sample may be physically or wirelessly delivered to a remote location. In some examples, samples are drawn into engagement with the sensor by a flexible tube that is attached to an outer surface of the UAV. The flexible tube may allow the UAV to precisely target and collect samples of dust and moisture and other materials from the ground over which the UAV operates.

20 Claims, 9 Drawing Sheets

ENVIRONMENTAL SAMPLING WITH AN UNMANNED AERIAL VEHICLE

TECHNICAL FIELD

The disclosure relates to collecting environmental samples with various types of aircraft including unmanned aerial vehicles.

BACKGROUND

An unmanned aerial vehicle (UAV) is an aircraft that flies without a human crew on board the aircraft. A UAV can be used for various purposes, such as reconnaissance, observation, thermal imaging, and the like. A micro air vehicle (MAV) is one type of UAV, which, due to its relatively small size, can be useful for operating in complex topologies, such as mountainous terrain, urban areas, and confined spaces. The structural and control components of a MAV are constructed to be relatively lightweight and compact.

SUMMARY

In general, this disclosure is directed to devices, systems, and techniques for collecting fluid samples with an unmanned aerial vehicle (UAV) in flight, as well as collecting samples of materials on the ground above which the UAV flies including samples of dust and other solid materials. In some examples described herein, a fluid sample device is configured such that it engages fluid sample(s) and/or ground sample(s) and then delivers quality characteristic information of the sample to another location.

In one example, a UAV includes a rotor fan, an engine, an annular duct, an avionics pod, and a fluid sample device. The engine is operatively connected to and configured to cause rotation of the rotor fan. The annular duct surrounds the fan. The rotation of the rotor fan causes a working fluid to be drawn through the duct to generate thrust to propel the UAV. The avionics pod is attached to an outer section of the annular duct. The fluid sample device is attached to the avionics pod and the fluid sample device further includes a sensor configured to detect a quality characteristic of a fluid that engages the sensor. The fluid sample device is arranged such that the working fluid drawn by the rotor fan through the duct engages the sensor.

In another example, the disclosure includes a method comprising flying a UAV to a location. The UAV in this method includes a rotor fan, an engine operatively connected to and configured to cause rotation of the rotor fan, an annular duct surrounding the fan, and an avionics pod attached to an outer section of the annular duct. The rotation of the rotor fan causes a working fluid to be drawn through the duct to generate thrust to propel the UAV. The method also includes collecting a sample of working fluid on a fluid sample device that is attached to the avionics pod. The fluid sample device includes a sensor that is configured to detect a quality characteristic of the fluid that engages the sensor. The fluid sample device is arranged such that the working fluid drawn by the rotor fan through the duct engages the sensor. The method includes flying the UAV to another location.

In another example, the disclosure includes a method comprising flying a UAV to a location. The UAV in this method includes a rotor fan, an engine operatively connected to and configured to cause rotation of the rotor fan, an annular duct surrounding the fan, an avionics pod attached to an outer section of the annular duct, and a fluid sample device that is attached to the avionics pod. The rotation of the rotor fan causes a working fluid to be drawn through the duct to generate thrust to propel the UAV. The fluid sample device comprises a sensor that is configured to detect a quality characteristic of a ground material that engages the sensor. The method also includes flying the UAV adjacent the ground and operating the UAV such that the working fluid flowing through the duct agitates the ground material. The method also includes collecting a sample of the ground material on the sensor through a flexible tube attached to an outer surface of the avionics pod. The tube is connected to an inlet of the fluid sampling device and configured such that the working fluid drawn by the rotor fan through the duct generates a pressure differential that causes the ground material to be drawn from a distal end of the tube into the fluid sampling device through the inlet and engage the sensor. The method includes flying the UAV to another location.

The details of one or more examples are set forth in the accompanying drawings and the description below. Other features, objects, and advantages of the disclosed examples will be apparent from the description and drawings, and from the claims.

BRIEF DESCRIPTION OF DRAWINGS

FIG. 5A is a top down view and FIG. 5B is a side view of the fluid sample device.

DETAILED DESCRIPTION

Figure 1:
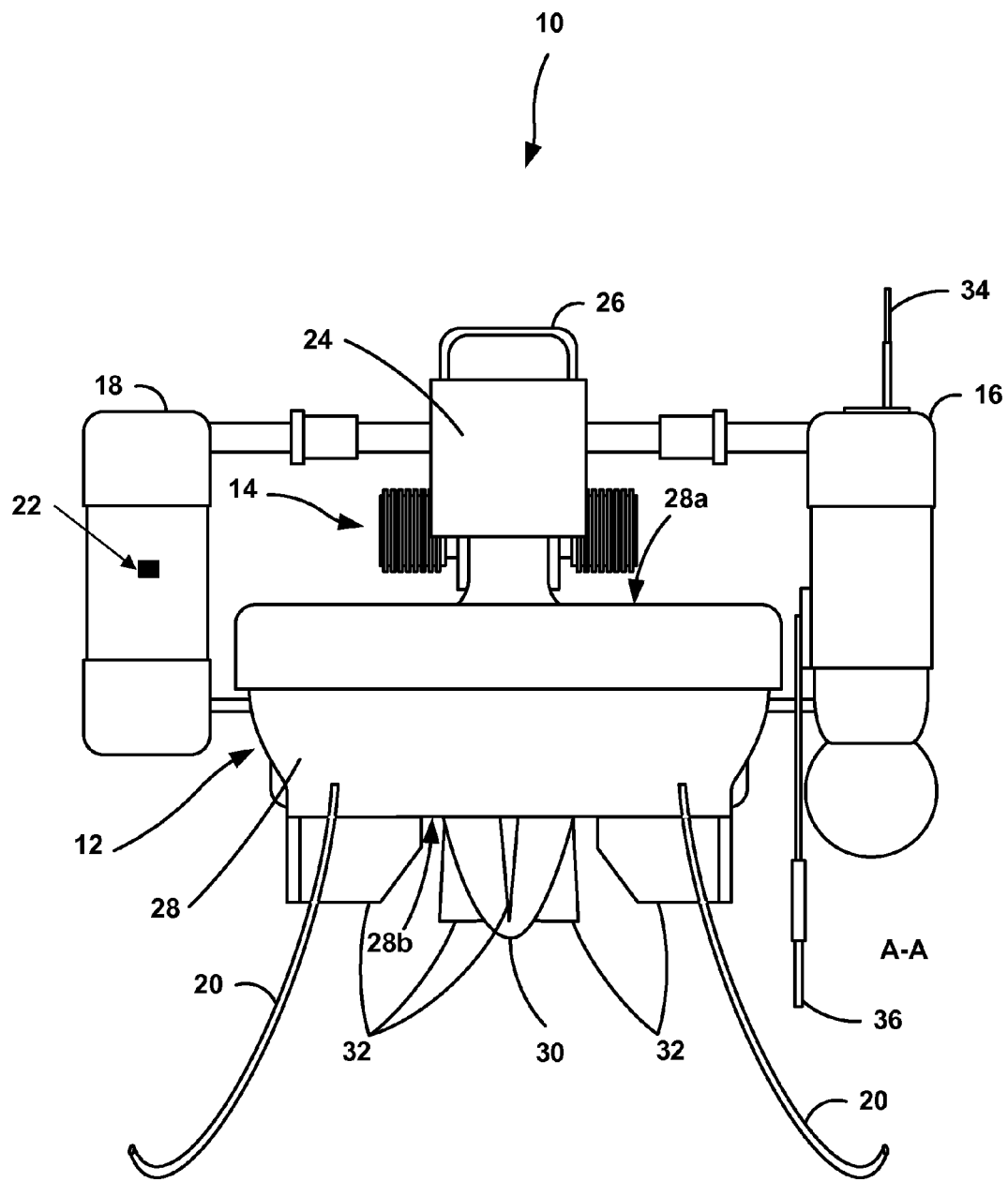
FIG. 1 is an elevation view of an example MAV.

While MAVs are primarily referred to herein, the devices, systems, and techniques for collecting fluid samples and samples of materials from the ground are applicable to any suitable UAV. A fluid sample, as used in this disclosure, may refer to any sample of gas, liquid, vapor, or particulate matter that has a quality characteristic detectable by a sensor and that may be present in the environment in which a MAV operates. A ground sample, as used in this disclosure, may refer to any gas, liquid, vapor, or particulate matter that is collected by a MAV according to this disclosure from the ground over which the MAV flies and that has a quality characteristic detectable by a sensor.

It can be useful to collect fluid samples and ground samples with a MAV because the samples may be located in remote locations and elevations that are problematic for collectors to reach. For example, such remote locations and elevations may be unreachable by humans, land vehicles, and water vehicles. Furthermore, the location of the fluid samples and ground samples may put the collector at risk of exposure to the potentially dangerous particulates or agents, which may lead to injury or death of the collector or the operator of the vehicle or device used to collect the samples.

It may be possible to equip a MAV with various types of devices, such as additional pumps or fans that are designed to generate flow of fluid samples to a fluid sample device included in the MAV. However, MAVs are designed to be lightweight and easily maneuverable, so it is important to avoid incorporation of any unnecessary components, which may diminish the MAV's performance. If a MAV were equipped with unnecessary components it may result in poor flying performance, which may result in inefficient and/or expensive operation, or other untoward consequences.

In other examples, a collector might collect fluid samples and ground samples under unregulated flow and pressure conditions. For example, a fluid sample device on a MAV may be configured to gather samples as the MAV is in motion through the air. However, some quality characteristics of fluid samples may be best detected under regulated flow and pressure conditions. As such, samples collected under unregulated flow and pressure conditions may lead to a false positive or negative of dangerous agents. The false indication may put other living and non-living collectors in danger or lead to unnecessary precautions and expense being taken to evacuate or secure the area. As such, it may also be useful to collect a metered amount of fluid samples and ground samples using a regulated flow and pressure of working fluid from a MAV. Additionally, it may be inconvenient or impossible to collect samples only while the MAV is propelled through the air. For example, for certain samples, such as ground samples, the MAV may be required to hover during collection.

In examples according to this disclosure, therefore, MAV's or other type of UAV's are equipped with a fluid sample device that includes a sensor configured to detect a quality characteristic of a fluid that engages the sensor and that is arranged such that a working fluid drawn by the rotor fan of the MAV through the duct engages the sensor. Thus, no additional equipment is required on the MAV to generate regulated flow of environmental fluids for sampling by the onboard sensor and the MAV can collect samples any time the rotor of the ducted fan of the MAV is operating, including in a hover flight mode.

A fluid sample device for a MAV that detects a quality characteristic of a fluid sample and/or ground sample is described with respect to FIGS. 1-8. In some examples, the MAV includes an avionics pod, which comprises a fluid sample device. The fluid sample device includes a sensor, an inlet door, an outlet door, and a motor. The motor is configured to actuate the opening and closing of both the inlet door and the outlet door, thereby allowing the working fluid that is drawn by the rotor fan of the ducted fan of the MAV through the duct to engage the sensor. The sensor is configured to detect a quality characteristic of the fluid and output a signal based on the quality characteristic.

In some examples, the MAV includes a flexible tube that is configured to hang from the MAV during flight. The flexible tube is configured to connect to an outer section of the avionics pod and attach to an inlet on the fluid sample device such that the working fluid drawn by the rotor fan through the duct generates a pressure differential that causes a fluid to be drawn from a distal end of the tube into the fluid sample device through the inlet and engage the sensor before being drawn out of the outlet of the fluid sample device.

The example MAV fluid sample device and methods described herein for detecting the quality characteristic of a fluid sample may result in safer detection of the presence of hazardous agents in fluid samples and ground samples. For example, the ability to detect the presence of hazardous agents with a MAV may require little to no interaction with such agents from people in the actual collection of the sample. Because samples may be located in remote or elevated locations, and the location of the sample may put the collector at risk of exposure to potentially dangerous particulates or agents, the limited interaction of people will promote the wellbeing and safety of those involved in the potentially dangerous task of retrieving samples. Furthermore, limiting the additional equipment to a fluid sample device, and, in some examples, a flexible tube, may help to minimize cost. In addition, limiting the additional equipment may minimize weight, which in turn may promote better operation of the MAV.

FIG. 1 is an elevation view of an example MAV 10 including ducted fan 12, engine 14, pods 16 and 18, landing gear 20, and fluid sample device 22. In FIG. 1, engine 14 is located toward the inlet end of ducted fan 12 and mechanically connected (either directly or indirectly) to the ducted fan. Pods 16 and 18 are offset laterally and connected to central console 24 that includes engine 14 and handle 26. In the example shown in FIG. 1, four landing gears 20 (only two are shown in the view of FIG. 1) are connected to ducted fan 12.

Engine 14 is operatively connected to and configured to drive ducted fan 12. In the example shown in FIG. 1, engine 14 is a reciprocating engine, and, in particular, a two cylinder internal combustion engine. However, other example MAVs may include other types of engines including, e.g., a gas turbine engine or electric motor. Engine 14 may be operatively connected to ducted fan 12 via an energy transfer apparatus, such as, but not limited to, a differential.

Ducted fan 12 includes duct 28, a rotor fan (not shown in FIG. 1), and tail cone 30. In some examples, ducted fan 12 will include both a rotor fan and stator fan. In such examples, the rotor fan, stator fan, and tail cone 30 may be arranged axially in the direction of flow through ducted fan 12 from duct inlet 28a to duct outlet 28b. In operation, the rotor fan of ducted fan 12 rotates to draw a working fluid including, e.g., air, into duct inlet 28a. The working fluid is drawn through the rotor fan, directed by the stator fan, if present, and accelerated out of duct outlet 28b around tail cone 30. The acceleration of the working fluid through duct 28 generates thrust to propel MAV 10 and control vanes 32 may be manipulated to direct the MAV along a particular trajectory, i.e., a flight path. In this manner, engine 14 drives ducted fan 12 to propel MAV 10 in flight. Duct 28 of ducted fan 12 may be formed of any suitable material including, e.g., various composites, aluminum or other metals, a semi rigid foam, various elastomers or polymers, aeroelastic materials, or even wood.

Although MAV 10 depicted in FIG. 1 includes one ducted fan 12, the number of ducted fans may vary in other example vehicles. In one example, a MAV may include two or more ducted fans 12. Various other features may also vary in other embodiments. In examples including an even number of ducted fans 12, each of the fans may be aligned side-by-side along a lateral plane (e.g., extending in a plane perpendicular to the plane of the image shown in FIG. 1).

Pods 16 and 18 of MAV 10 may include, e.g., payload and avionics pods. In one example, pod 16 may be configured to transport various types of payloads for any number of missions for MAV 10, including, e.g., objects to be dropped or placed by the MAV. In the example of FIG. 1, pod 16 also includes communications antennae 34, 36, which may be configured for radio and video communications, respectively, to and from MAV 10. Additionally, pod 18 may be configured to carry an avionics package including, e.g., avionics for communicating to and from MAV 10, navigating the MAV, as well as flight control electronics and sensors. In some examples, pods 16, 18 can also be switched, such that pod 16 includes avionics and pod 18 includes a payload. As described in greater detail below, pod 18 also includes fluid sample device 22 configured to collect fluid samples from the environments in which the MAV 10 operates and detect quality characteristics of such samples.

Landing gear 20 of MAV 10 are formed as elongated rods with curved feet configured to engage a landing surface and may be fabricated from a variety of materials including metals, plastics, and composites. In some examples, landing gear 20 may be fabricated from one or more materials that exhibit some inherent resiliency to cushioning the MAV during landings. Other example MAVs may include fewer or more landing gear 20, which may be connected to different components of the vehicle than shown in the example of FIG. 1.

In the example of FIG. 1, MAV 10 may also include one or more sensors and handle 26. In some examples, sensors may be attached, e.g., to avionics pod 18, and configured to sense objects and/or other conditions surrounding MAV 10 and to facilitate operation thereof. For example, MAV 10 may include sensors that sense the attitude and air speed of the vehicle, as well as ambient air pressure and temperature. MAV 10 may have sensors disposed in other positions relative to the components of the vehicle. For example, pressure sensors may be mechanically connected to and distributed around a lip of duct 28 of ducted fan 12 (e.g., evenly or unevenly space around the lip of duct 28).

Handle 26 is attached to, coupled to, or formed integral with central console 24 that includes engine 14. Handle 26 may generally be used to move MAV 10 off of a starter after engine 14 of the aircraft is running. Handle 26 may also be configured to assist with capture of MAV 10, for example, by being engaged by a non-depicted capture device. In the example depicted in FIG. 1, handle 26 protrudes out from central console 24. However, in other examples, handle 26 may be implemented as a pocket or other recess in central console 24. In addition, in some examples, MAV 10 does not include handle 26.

Pods 16 and 18 further include vents, which are not shown in FIG. 1. The vents are configured to allow working fluid drawn by the rotor fan through the duct to draw fluid through the vents. The fluid flow through the vents is intended to cool various internal components of pods 16 and 18. For example, the fluid flow provides cooling air to an electrical stack located in avionics pod 16.

In the example shown in FIG. 1, pod 18 includes fluid sample device 22. In particular, fluid sample device 22 resides within a vent in pod 18. In this manner, pod 18 is configured such that working fluid drawn by the rotor fan through duct 28 engages fluid sample device 22. Fluid sample device 22 is configured to detect a quality characteristic of the fluid sample and, in some examples, autonomously deliver the quality characteristic of the sample to another location. The vent is configured such that no additional equipment (e.g. an impeller) is required in order to cause fluid drawn by the rotor fan through duct 28 to engage fluid sample device 22. In other examples, however, MAV 10 may include additional equipment in the form of a flexible tube that is attached to an outer surface of pod 18 and that is configured to facilitate collection of samples from the ground over which MAV flies.

In one example, one or both of avionics pod 18 and payload pod 16 include a fluid sample device. In yet another example, a plurality of fluid sample devices is attached to various places on MAV 10 such that working fluid drawn by the rotor fan of ducted fan 12 through duct 28 engages fluid sample devices.

Figure 2:
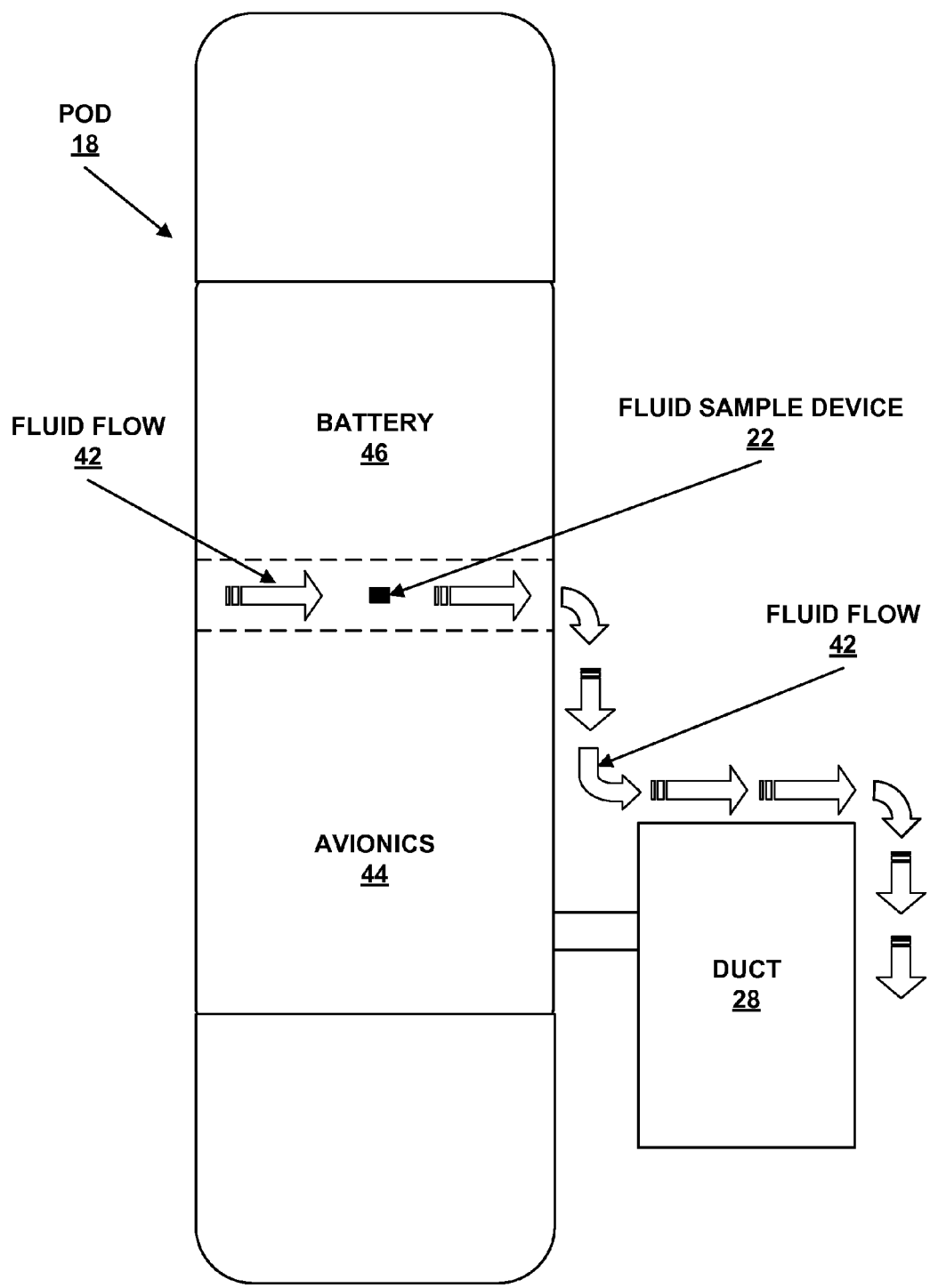
FIG. 2 is a conceptual diagram of an avionics pod, a fluid sample device, an annular duct, and a fluid flow through the fluid sample device.

FIG. 2 is a conceptual diagram of avionics pod 18, fluid sample device 22, duct 28, and fluid flow 42. FIG. 2 illustrates the path that cooling air (or other working fluid), or fluid flow 42 drawn by the rotor fan takes through a vent of avionics pod 18, across fluid sample device 22, and then through duct 28. FIG. 2 illustrates that fluid sample device 22 collects fluid samples using existing fluid flow 42 that is already being drawn by the rotor fan through duct 28. In this manner, no additional equipment is required in order to create fluid flow 42 across fluid sample device 22.

FIG. 2 illustrates that avionics pod 18 is attached to an outer surface of duct 28 and is configured to allow fluid flow 42 to flow through avionics pod 18. Fluid sample device 22 resides in a location within avionics pod 18 such that fluid flow 42 engages fluid sample device 22 as it is drawn through pod 18 and duct 28 by the rotor fan of the ducted fan of the MAV. Particularly, in FIG. 2, fluid sample device is horizontally (in the orientation illustrated in FIG. 2) located in the center of pod 18, and vertically (in the orientation illustrated in FIG. 2) located above avionics 44 and below battery 46. In this manner, fluid sample device 22 is able to use the existing fluid flow 42 to collect samples and detect quality characteristics of fluids present in the environment in which MAV 10 operates.

Fluid sample device 22 may be electrically connected to battery 46. In doing so, fluid sample device 22 may draw any power necessary for operation of the device from battery 46, e.g., to power a sensor of the device and/or to operate one or more motors configured to open and close inlet and outlet doors of the fluid sample device. Furthermore, fluid sample device 22 may also be electrically connected to avionics 44. In this manner, avionics 44 may receive fluid quality characteristics detected by a sensor included in fluid sample device 22. Avionics 44 may then store the detected quality characteristics in memory 48 and/or wirelessly transmit the quality characteristics to another location.

In other examples, fluid sample device 22 may be arranged in a number of different locations other than the one illustrated in FIG. 2. For example, fluid sample device 22 may be arranged a different location horizontally along the path of fluid flow 42 within pod 18. Additionally, fluid sample device 22 may be arranged in other locations inside pod 18, or even adjacent to pod 18, such that fluid sample device 22 is still located along the path of fluid flow 42. In general, fluid sample devices according to this disclosure may be attached to any existing structure of an MAV such that the flow of fluid drawn by the rotor of the ducted fan of the MAV is drawn through the fluid sample device.

Figure 3:
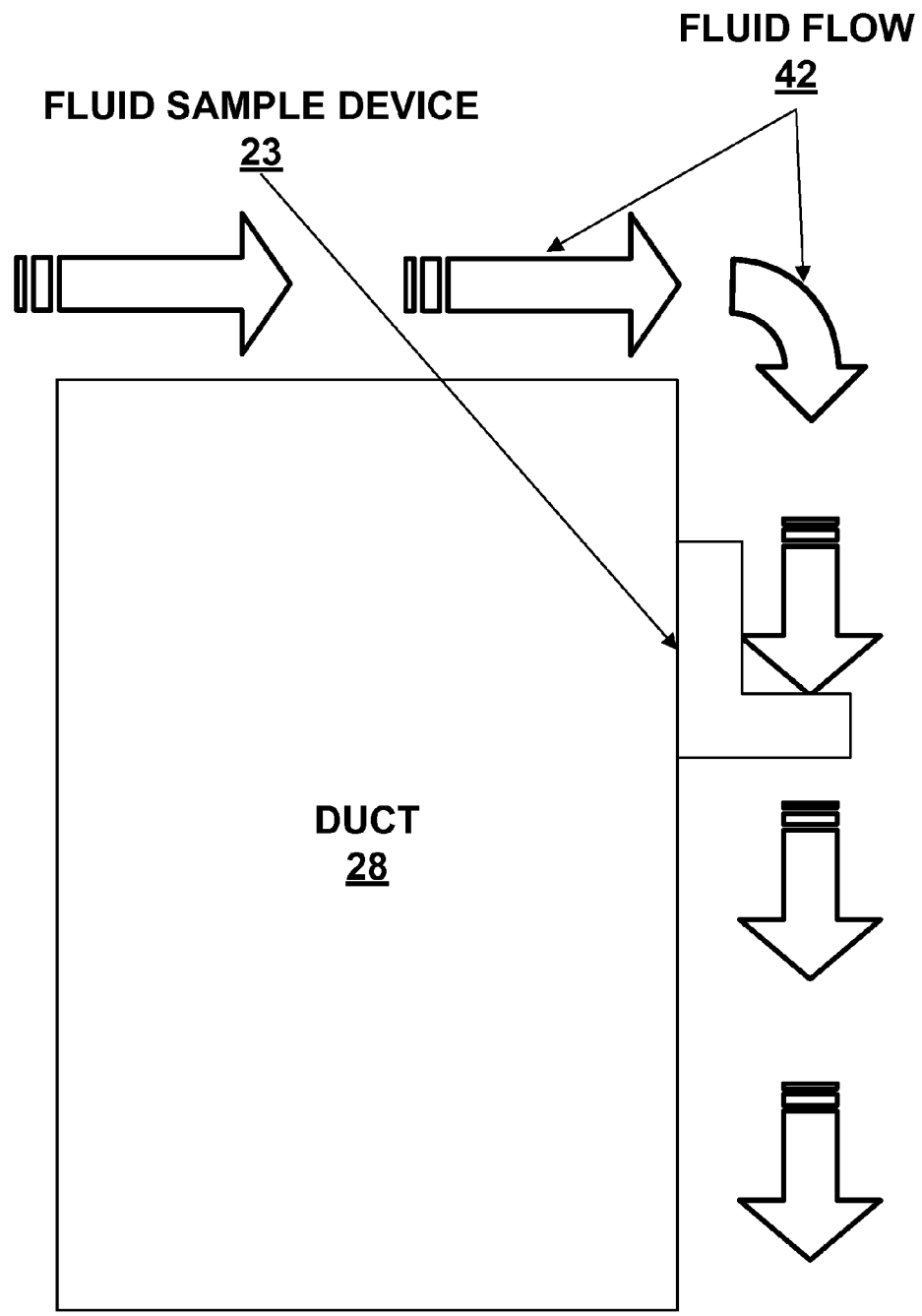
FIG. 3 is a conceptual diagram of another example fluid sample device arranged on the duct of a ducted fan MAV.

For example, FIG. 3 is a conceptual diagram that illustrates another example of fluid sample device 23 as being an "L" shaped device. In this example, fluid sample device 23 is attached to duct 28, instead of pod 18, as illustrated in FIG. 2. Specifically, the leg of the "L" of fluid sample device 23 that runs vertically, with respect to duct 28, is attached to duct 28. In this manner, the leg of the "L" of fluid sample device 23 that runs horizontally, with respect to duct 28, is located one-half to one inch below a lip of duct 28. The location and configuration of the "L" shaped fluid sample device 23 is intended to capture the high flow rate experienced at and around the lip of duct 28, or, in other words, the inlet of the duct.

Referring again to FIG. 2, in one example, when the rotor fan of the ducted fan of the MAV is spinning at a maximum or near maximum rotation, fluid flow 42 is about 1.5 cubic feet per minute. However, fluid flow 42 may be more or less depending on the speed of rotation of the rotor fan. In another example, fluid sample device 22 may be configured to further regulate fluid flow 42 that travels through an interior section of fluid sample device 22. Regulating fluid flow 42 may be necessary for the detection of quality characteristics of specific fluid samples. For example, fluid sample device 22 may include inlet and outlet doors that may be operated to open and close to varying degrees to meter fluid flow through the interior of the device.

Fluid sample device 22 may be constructed from a number of different kinds of plastic, which has the ability to be easily cleaned and is robust enough for multiple uses. In another example, fluid sample device 22 is a metallic structure that may be selected specifically for exposure to certain fluid samples. In another example, fluid sample device 22 is made of any of a number of different types of corrosion resistant material.

Figure 4:
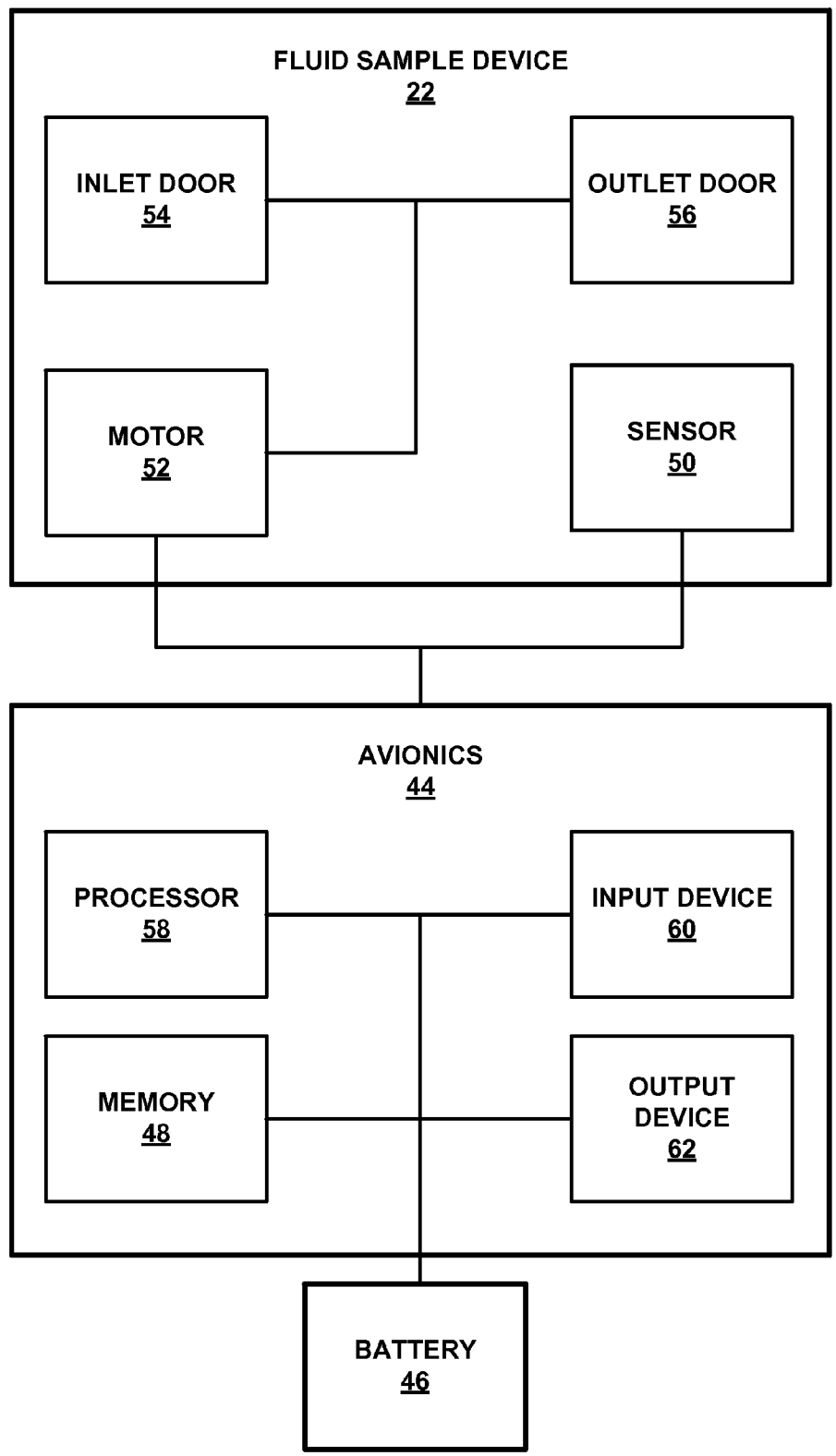
FIG. 4 is a conceptual diagram of a fluid sample device and avionics.

FIG. 4 is a schematic view of fluid sample device 22 and avionics 44. In one example, such as the examples of FIGS. 1 and 2, both fluid sample device 22 and avionics 44 reside within avionics pod 18. In another example, fluid sample device 22 is arranged separate from avionics 44 in pod 18 and the components are communicatively connected. For clarity, the other components of MAV 10 and ducted fan 12 have been removed in FIG. 4. As illustrated in FIG. 4, example fluid sample device 22 includes sensor 50, motor 52, inlet door 54, and outlet door 56. Example avionics 44 includes memory 48, processor 58, input device 60, and output device 62. FIG. 4 is intended to show how the various electrical, mechanical, and logical connections of the different components of fluid sample device 22 and avionics 44 work together to detect quality characteristics of a fluid sample that engage sensor 50. In other examples according to this disclosure, a fluid sample device and avionics may include fewer or more components.

In FIG. 4, inlet door 54 and outlet door 56, of fluid sample device 22, are mechanically connected to motor 52. Motor 52 is configured to actuate the opening and closing of inlet door 54 and outlet door 56, e.g. via command received by an MAV from a ground station command or a pre-programmed set of instructions. The inlet door is located on a first side of the fluid sample device and an outlet door is located on a second side of the fluid sample device, wherein the second side opposes the first side. When inlet door 54 and outlet door 56 are opened this may allow a fluid sample and/or ground sample to flow through fluid sample device 22 and engage sensor 50. The inlet door and outlet door are configured to be adjusted to control the fluid flow to an interior section of the fluid sample device. The physical configuration of fluid sample device 22 including inlet and outlet doors is described in greater detail below with reference to FIGS. 4A and 4B.

Motor 52 is electrically connected to avionics 44. The electrical connection of motor 52 to avionics 44 is configured so that motor 52 receives electrical signals from processor 58 and/or an input/output card that control motor 52 to actuate the opening and closing of inlet door 54 and outlet door 56. Motor 52 is also connected to battery 46, directly or indirectly through avionics 44, so that motor 52 may draw any necessary power, to actuate the opening and closing of inlet door 54 and outlet door 56. Aside from motor 52, battery 46 may also power other components, including those components shown in the schematic of FIG. 4, such as memory 48, sensor 50, processor 58, input device 60, and/or output device 62.

One aspect of inlet door 54 and outlet door 56 is that the doors may be able to be actuated autonomously, e.g. via a wireless ground station command or a pre-programmed set of instructions. The doors may also be configured to operate independently of each other. Additionally, the independent actuation of inlet door 54 and outlet door 56 may also allow fluid flow 42 (see FIGS. 2 and 3) and pressure to be regulated based upon the openings of inlet door 54 and outlet door 56. In this manner, regardless of the speed of rotation of the rotor fan, fluid sample device 22 is able to control fluid flow rate and pressure as necessary to detect certain quality characteristics of fluid samples. Additionally, the ability to regulate fluid flow and pressure may simply promote increased efficacy and accuracy of different types of sensor 50 in detecting quality characteristics of fluid samples.

In one example, sensor 50 and motor 52 communicate wirelessly with avionics 44, via telemetry or any other wireless device. In this manner, there is no wired electrical connection from sensor 50 and motor 52 to avionics 44. In this scenario, fluid sample device 22 may contain its own independent power source (e.g. a battery); either located within fluid sample device 22 or somewhere else within pod 18. As such, in some examples, fluid sample device 22 may not require any power from battery 46.

In another example, fluid sample device 22 may not contain an independent power source, and may wirelessly draw power from battery 46 or another power source. In one example, fluid sample device 22 may not have any electrical connections from sensor 50 and motor 52 to avionics 44, and command signals and power may be transmitted wirelessly between fluid sample device 22 and avionics 44.

In another example, fluid sample device 22 does not have any electrical connections with avionics 44 and does not receive any wireless command signals and power from avionics 44. For example, fluid sample device 22 may receive power and transmit and receive command signals from another component of MAV 10 or from a remote operator and/or device.

In FIG. 4, avionics 44 may be implemented, at least in part, by hardware, software, firmware or any combination thereof. Although FIG. 4 schematically illustrates avionics 44 as including memory 48, processor 58, input device 60, and output device 62, one or more of these components may be logically and/or physically isolated from avionics 44. In one example, battery 46, memory 48, processor 58, input device 60, and output device 62 reside in various locations in and around MAV 10. In another example, one or more of memory 48, processor 58, input device 60, and output device 62 reside at one or more remote locations.

The example in FIG. 4 illustrates that avionics 44 includes processor 58. Processor 58 is electrically connected to fluid sample device 22, as well as other components of avionics 44, including memory 48, input device 60, and output device 62, and battery 46. Processor may include one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. Processor 58 may be configured to carry out the instructions of a computer program and/or sequences of instructions to perform arithmetical, logical, and/or input and output operations of avionics 44.

In the example of FIG. 4, processor 58 may instruct fluid sample device 22 to perform various operations. For example, processor 58 may instruct motor 52 when to actuate the opening and closing of inlet door 54 and outlet door 56. For example, processor 58 may contain instructions that command motor 52 to actuate opening and closing of the doors when MAV 10 hovers at a target altitude. In another example, processor 58 may instruct motor to actuate the doors when MAV 10 is located at a targeted coordinate determined using a global position system (GPS) included in avionics 44. In another example, processor 58 may instruct motor to actuate the doors when the rotation of the rotor fan reaches a target speed of rotation.

Processor 58 may also execute instructions related to the operation of sensor 50. For example, processor 58 may instruct sensor to detect a specific quality characteristic of a certain fluid sample. Processor 58 may also instruct sensor 50 to detect quality characteristics of the fluid sample for a target amount of time or level of exposure of sensor 50 to a fluid sample. In this manner, processor 58 may instruct sensor 50 to be active or inactive at different times. Processor 58 may also be configured to receive electrical signals from sensor 50 that represent levels and types of quality characteristics of the fluid sample that engage sensor 50. Upon receipt of these electrical signals, processor 58 may then instruct sensor to remain active and continue measuring quality characteristics of the fluid sample, or, depending on the electrical signal from sensor 50, processor 58 may instruct sensor to stop collecting samples and effectively become inactive.

Avionics 44 also includes memory 48. Memory 48 is electrically connected to processor 58, input device 60, output device 62, battery 46, and fluid sample device 22. Memory 48 may be implemented as Flash memory, random access memory (RAM), or any other type of volatile or non-volatile memory that stores data. In one example, memory 48 is configured to store one or more quality characteristics of a fluid sample collected by sensor 50. Memory 48 may also store programs and/or sequences of instructions for execution by processor and/or for controlling sensor 50, motor 52, inlet door 54, and outlet door 56. In one example, memory 48 contains programs and/or sequences of instructions that instruct processor 58 to perform various operations. Memory 48 may be pre-loaded with programs and/or instructions before the MAV begins its flight. Memory 48 may also be configured to wirelessly transmit and receive programs and/or instructions to/from a remote location, e.g. from a ground station. In this manner, memory 48 may be updated with new programs and/or instructions after MAV 10 has begun its flight.

The example shown in FIG. 4 also includes input device 60 and output device 62. Input device 60 and/or output device 62 may be electrically, mechanically, or operatively connected to each other and/or avionics 44. Input device 60 may include one or more of a camera, radio frequency receiver, laser rangefinder, GPS receiver, compact disc (CD), microphone, or any other type of direct or indirect input device. Output device 62 may include one or more communication devices, speakers, monitors, or any type of hardware equipment used to communicate electrical signals from or other information related to sensor 50, motor 52, processor 58, input device 60, memory 48, and battery 46.

Figure 5A:
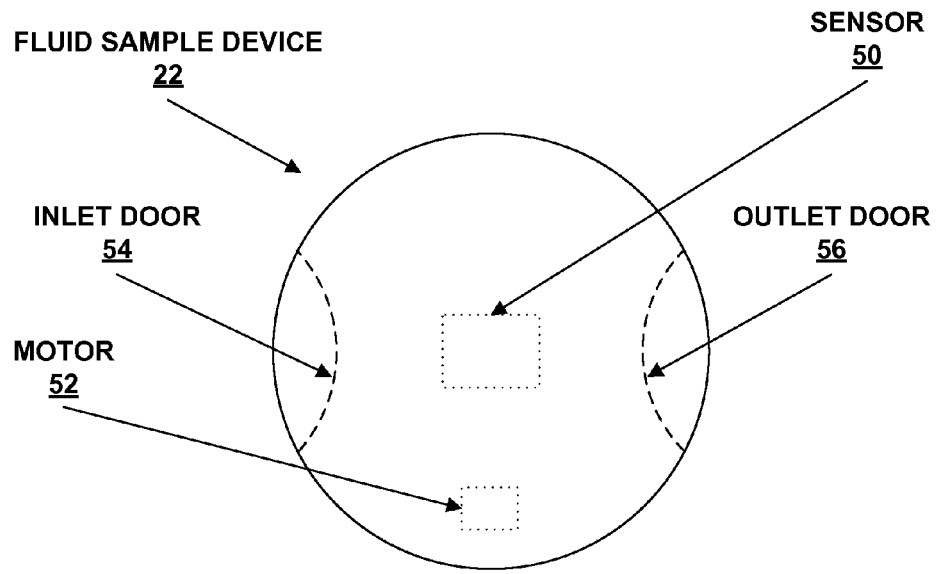
FIGS. 5A and 5B illustrate two different views of a fluid sample device.
Figure 5B:
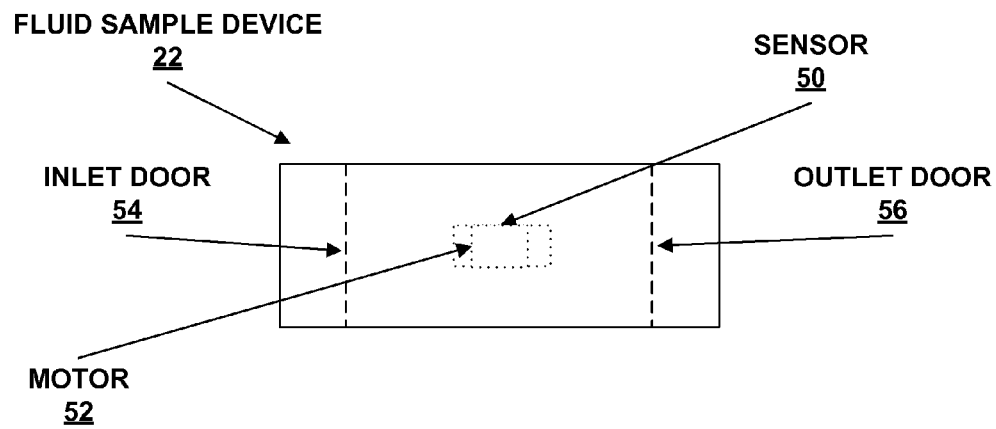
Figure 6:
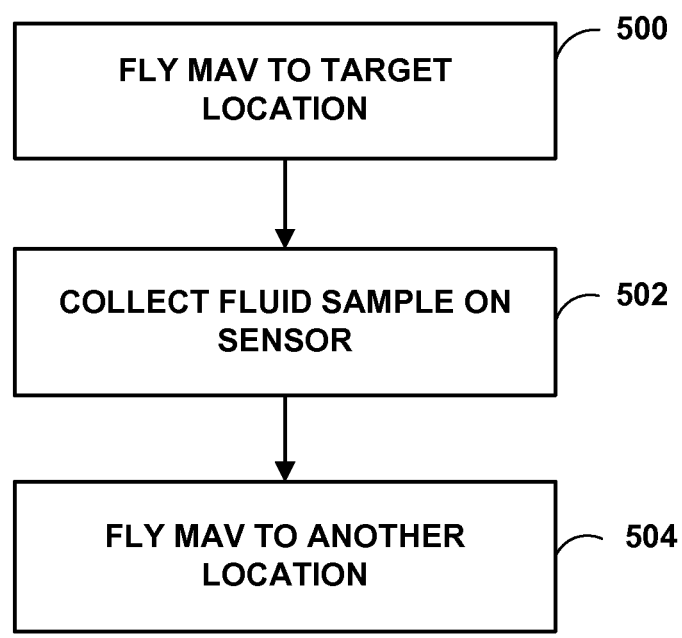
FIG. 6 is a flow chart illustrating a method of detecting a quality characteristic of an air and/or gas sample using a MAV.
Figure 7:
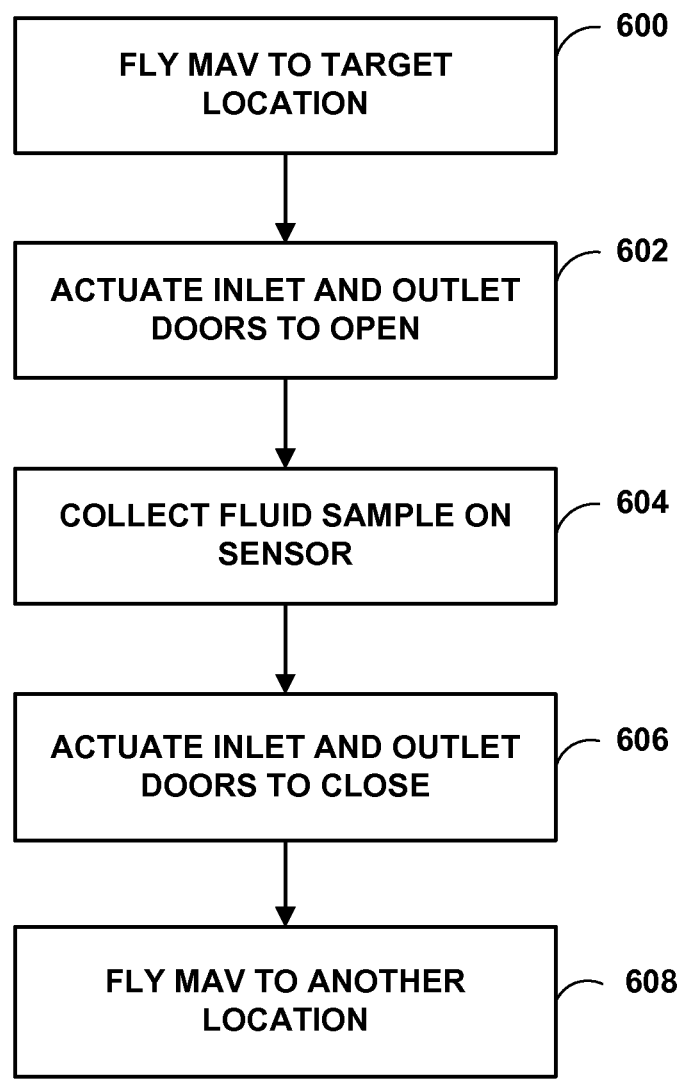
FIG. 7 is a flow chart illustrating a more detailed example method of detecting a quality characteristic of an air and/or gas sample using a MAV.

FIGS. 5A and 5B illustrate two different views of fluid sample device 22. Specifically, FIG. 5A is a top down view and FIG. 5B is a side view of fluid sample device 22. In the example shown, fluid sample device 22 includes inlet door 54, outlet door 56, sensor 50, and motor 52. Inlet door 54 and outlet door 56 are located on an exterior surface of fluid sample device 22, with the doors being laterally offset from each other. Sensor 50 and motor 52 reside in an interior portion of fluid sample device 22. In another example, motor 52 may be arranged outside of the interior of or apart from fluid sample device. FIGS. 5A and 5B are intended to illustrate how fluid sample device 22 operates and to show its general shape in examples in which such a device is included in an avionics or payload pod of an MAV or other type of UAV.

In the example of FIGS. 5A and 5B, fluid sample device 22 is puck-shaped and relatively small in size, as compared to MAV 10. The small relative size of fluid sample device 22 is necessary to both minimize extra weight that is added to MAV 10 and also to reduce interference with fluid flow 42 that is drawn by the rotor fan through the duct to propel MAV 10. However, different shapes and sizes of fluid sample device 22 may be implemented based on different types and sizes of sensor 50, motor 52, inlet door 54, and outlet door 56, as well as the particular location on or in the MAV the device is arranged.

Sensor 50 is attached to an interior portion of fluid sample device 22. Particularly, sensor 50 may be attached to fluid sample device 22 by any mechanical means, such as friction fit, adhesive mount, screw fastener, or any other type of permanent or non-permanent mounting option. The purpose of sensor 50 is to detect a quality characteristic of a fluid sample that engages sensor 50. As such, in the example illustrated in FIGS. 4A and 4B inlet door 54 and outlet door 56 must be opened in order to allow a working fluid drawn by the rotor fan through the duct to engage sensor 50. The inlet door and outlet door may be opened at the same or different levels. As such, inlet door 54 and outlet door 56 may be actuated independent to each other. The purpose of opening inlet door 54 and outlet door 56 at the same or different levels is to control the pressure and fluid flow rate across sensor 50. Particular quality characteristics of certain fluids may require differing fluid flow rates in order to engage sensor 50 to detect the characteristic. Additionally, inlet door 54 and outlet door 56 allow for fluid flow 42 to flow through fluid sample device 22. In this manner, fluid sample device 22 experiences decreased wind resistant, which reduces the likelihood of fluid sample device 22 breaking off of avionics pod 18 and causing damage to MAV 10.

Motor 52 also resides in an interior portion of fluid sample device 22. FIGS. 5A and 5B illustrate that motor 52 is smaller than sensor 50; however, in other examples, motor 52 may be larger than sensor 50. Motor 52 is mechanically connected to inlet door 54 and outlet door 56. Motor 52 may be any of a number of different types of electric motors that fit in a relatively small space. In one example, motor 52 is a servomotor that may be paired with some type of encoder to provide position and/or speed feedback in regards to the motor's operation. In another example, motor 52 is a stepper motor that is able to precisely actuate the opening and closing of inlet door 54 and outlet door 56 to specific angular positions.

Inlet door 54 is located on a first side of fluid sample device 22 and outlet door 56 is located on a second side of fluid sample device 22, wherein the second side generally opposes the first side. Inlet door 54 and outlet door 56 may be configured in a variety of different types and shapes. In the example of FIGS. 5A and 5B, inlet door 54 and outlet door 56 are c-shaped and slide up and down, similar to a louver. In another example, one or both of inlet door 54 and outlet door 56 roll along a system of tracks guided by rollers, similar to a garage door, to open and close independent to each other. In yet another example, one or both of inlet door 54 and outlet door 56 are attached to an annulus that rotates to cause one or both doors to open and close independent to each other. The person of ordinary skill in the art will recognize that inlet door 54 and outlet door 56 may be a variety of different shapes and types.

Inlet door 54 and outlet door 56 may be constructed from a number of different kinds of plastic, which may be easily cleaned and robust enough for multiple uses. In another example, inlet door 54 and outlet door 56 are metallic or another type of generally rigid material that is resistant to corrosion.

The example shown in FIGS. 5A and 5B also includes sensor 50, which resides in an interior portion of fluid sample device 22. In FIGS. 5A and 5B sensor 50 is configured to detect a quality characteristic of a fluid sample that is drawn by the rotor fan of an MAV through the duct and enters in to fluid sample device 22 once inlet door 54 and/or outlet door 56 are actuated to open.

Sensor 50 may take a number of different forms. In one example, sensor 50 is one or more single-use collection membranes that detect quality characteristic and change colors based on the presence or absence of a particular quality characteristic. In one example, sensor 50 includes a collection membrane that is all white when MAV 10 departs on its mission, and once the collection membrane has detected a certain quality characteristic, for example an acid, the collection membrane may become all purple. The change in color notifies personnel that the collection membrane was exposed to a particular acid. This is just one of the many examples of how sensor 50 may include a collection membrane that detects and subsequently indicates the presence of a certain quality characteristic. In the foregoing examples, the collection membrane is a single-use device, so once the membrane has been contaminated or exposed to any fluid sample, the membrane will be disposed of and may be replaced with a different sensor, e.g., another collection membrane.

In another example, sensor 50 may include a collection membrane only a portion of which changes colors when exposed to a certain quality characteristic of the fluid sample. In this manner, personnel will not have to remember what color the collection membrane was when it was installed in fluid sample device 22. For example, personnel might forget if white or purple represents no exposure or contamination, which may create confusion. In this example, personnel will only have to know that if the collection membrane shows two or more colors on the collection membrane to determine that detection of a quality characteristic has occurred. This may avoid mistakes with regard to what different colors represent.

In another example, sensor 50 includes a collection membrane that displays characters, such as letters or numbers, to indicate whether the collection membrane has detected a quality characteristic. For example, the collection membrane may have the word "GOOD" displayed, and upon detection of a certain quality characteristic of a fluid sample, the collection membrane then displays "BAD." A variety of additional indication methods may be employed to notify personnel whether the collection membrane has been exposed to a certain quality characteristic.

Sensor 50 including one or more collection membrane(s) may also be attached to fluid sample device 22 in a number of different ways. In one example, the collection membrane is attached to fluid sample device 22 by a hook-and-loop fastening system. In another example, the collection membrane is adhesively attached, using a non-permanent tape, glue, or epoxy. In yet another example, the collection membrane is attached magnetically.

In other examples, sensor 50 may also be a multiple-use electronic sensor that detects specific types of chemical, biological, radiological, nuclear, and/or explosive quality characteristics. In one example, sensor 50 may be one of a chemical, biological, radiological, nuclear, or explosive sensor. For example, sensor 50 may be an electronic sensor that only detects chemical quality characteristics. In another example, sensor 50 is an electronic sensor that only detects biological quality characteristics. In another example, sensor 50 is an electronic sensor that only detects radiological quality characteristics. In another example, sensor 50 is an electronic sensor that only detects nuclear quality characteristics. In yet another example, sensor 50 is an electronic sensor that only detects explosive quality characteristics. Having fluid sample devices that are configured to detect specific quality characteristics may reduce the size and cost of fluid sample devices in accordance with this disclosure.

The sensor may be a multiple-use electronic sensor that is configured to detect changes in electric or magnetic signals based on a fluid sample and/or ground sample. In one example, the electronic sensor may generate its own voltage through a chemical reaction between a fluid sample and/or ground sample and a catalyst contained in the electronic sensor. The electronic sensor may indicate a quality characteristic of the fluid and/or ground sample that is associated with an electric or magnetic signal. In another example, the electronic sensor may produce a current in response to the concentration of a quality characteristic of a fluid sample and/or ground sample that engages the electronic sensor. For example, in detecting carbon monoxide, the electronic sensor may contain a plurality of electrodes that are immersed in an electrolyte solution. Carbon monoxide may be oxidized to carbon dioxide at one electrode while oxygen is collected at another electrode. The presence of these elements on the two electrodes may create an electric circuit, which indicates the presence of the quality characteristic of carbon monoxide.

In one example, sensor 50 is a spectrometer. In this example, sensor 50 is configured to measure a spectrum of light that is reflected off specific chemicals, in a gas, vapor or liquid phase. Sensor 50 may be further configured to determine the type, concentration, and/or quantity of the specific chemical based on the spectrum of light reflected off of the chemical in the sample.

In another example, sensor 50 is able to detect multiple of chemical, biological, radiological, nuclear, and/or explosive quality characteristics. In yet another example, sensor 50 is a chemical, biological, radiological, nuclear, and explosive (CBRNE) sensor, wherein sensor 50 is able to detect any of the chemical, biological, radiological, nuclear, and explosive quality characteristics.

In one example, the quality characteristic detected by sensor 50 is sulphur dioxide, any oxide of nitrogen, ozone, carbon monoxide, carbon dioxide, hydrogen sulphide, nonmethane hydrocarbon, benzene, toluene, xylene, lead, ammonia, methane, solar radiation, suspended particulate matter, or any respirable particulate matter.

Sensor 50 may also transmit and receive signals via telemetry or any other wireless method. In this manner, the electronic sensor may able to wirelessly communicate quality characteristic data to a third party or to another component located within avionics pod 18. Furthermore, electronic sensor may also be able to receive instructions or programs from a third party, or any other avionics component.

Sensor 50 may be attached to fluid sample device 22 by any permanent or non-permanent mechanism. In one example, if electronic sensor 50 is permanently attached, then this configuration may result in a specific fluid sample device for each quality characteristic application. For example, there may be a chemical fluid sample device, a biological fluid sample device, a radiological fluid sample device, etc. In this manner, MAV 10 may be equipped with the specific fluid sample device that is required to detect the necessary quality characteristic. For example, in the event of a malfunction at a nuclear power plant, MAV 10 may be equipped with a nuclear fluid sample device. In this scenario, MAV 10 will be able to detect quality characteristics related to nuclear radiation, such as, but not limited to, alpha particles, beta particles, and/or gamma rays. Additionally, the fluid sample device, e.g., fluid sample device 22 as a whole versus just sensor 50, may be configured to be removed and swapped out of MAV 10 depending on the mission.

Sensor 50 may also be attached to fluid sample device 22 by any non-permanent mechanism, such as hook-and-loop fastening, adhesive tape, or a friction fit with fluid sample device 22. In this manner, fluid sample device 22 may be used to detect multiple quality characteristics, by swapping different sensors out for one another. For example, using the non-permanent attachment method, if after MAV 10 returns from the malfunctioning nuclear power plant and is then going to be deployed to a suspected biological warfare area, fluid sample device 22 may be equipped with an electronic sensor that detects biological quality characteristics. In this manner, MAV 10 is equipped with the same fluid sample device 22, but MAV 10 is now able to detect biological quality characteristics, instead of nuclear.

In another example, electronic sensor 50 is able to detect a plurality of chemical, biological, radiological, nuclear, and explosive quality characteristics. In this manner, fluid sample device 22 may require little to no additional retrofitting to measure any of a number of different quality characteristics. For example, in the example described above, MAV 10 may be able to fly to the nuclear power plant where it detects the nuclear quality characteristics, and then immediately fly to the suspected biological warfare area to detect biological quality characteristics.

In the example shown in FIGS. 5A and 5B, sensor 50 is either one or more collection membrane(s) or an electronic sensor. Although, in another example, sensor 50 contains both one or more collection membrane(s) and an electronic sensor or a plurality of electronic sensors.

FIG. 6 is a flow chart illustrating a high-level example method of detecting a quality characteristic of a fluid sample using MAV 10. In the method of FIG. 6, MAV 10 flies to a target location (500). The target location may be a predetermined location or an improvised location. A predetermined location may be a programmed instruction that is stored in memory 48 at the time that MAV initiates its flight sequence. The target location may also be an improvised location that is transmitted to MAV 10 via a wireless communication that is received by avionics 44. For example, MAV 10 may be piloted by an operator at a ground control station to the location without the particular location being stored in memory or determined by a processing device of the MAV. The target location may also be a location that MAV 10 determines via processor 58.

MAV 10 collects a fluid sample on sensor 50 (502) and then flies to another location (504). In doing so, MAV 10 may repeat the entire method as illustrated in FIG. 6, or MAV 10 may fly to any other remote location to report the quality characteristic of the ground material or moisture sample.

In one example, sensor 50 may be configured to wirelessly transmit the quality characteristic of a fluid sample to a remote location. Sensor 50 may perform a self-cleaning operation that enables MAV 10 to collect other quality characteristic(s) of fluid sample(s) during the same flight sequence. For example, sensor 50 may use high frequency vibrations to remove a fluid sample and/or ground sample from a surface of sensor 50. Sensor 50 may implement any number of different self-cleaning operations. In this manner, MAV 10 may fly to multiple other locations to retrieve quality characteristic information from other fluid samples. MAV 10 may also fly to a location where the quality characteristic information of a fluid sample is physically or electronically retrieved from fluid sample device 22.

FIG. 6 is a flow chart illustrating another example method of detecting a quality characteristic of a fluid sample using MAV 10. Like FIG. 6, the functions of the method of FIG. 6 for detecting a quality characteristic of a fluid sample are described as carried out by the various components as shown by the examples in FIGS. 1-6.

In the example in FIG. 7, MAV 10 flies to a target location (600). Like the example in FIG. 6, the target location may be a programmed instruction that is stored in memory 48 at the time that MAV initiates its flight sequence. The target location may also be transmitted to MAV 10 via a wireless communication that is received by avionics 44. For example, MAV 10 may be piloted by an operator at a ground control station to the location without the particular location being stored in memory or determined by a processing device of the MAV. The target location may also be a location that MAV 10 determines via processor 58.

The inlet door and outlet door then actuate to open (602). Inlet door 54 and outlet door 56 may be actuated to open to varying degrees, in other words, the size of the opening formed by the inlet and outlet doors may vary. In such a case, inlet door 54 and outlet door 56 may be configured to control the fluid flow rate and pressure that flows through fluid sample device 22. In another example, inlet door 54 and outlet door 56 are actuated to completely open. Additionally, inlet door 54 and outlet door 56 may be actuated to open, whether to the same or varying degrees, independent of one another.

Next, sensor 50 within fluid sample device collects a fluid sample (604). This is caused by the rotor fan of MAV through duct 28 generating a pressure differential across the two sides of avionics pod 18 including inlet door 54 and outlet door 56, which draws working fluid into the interior of fluid sample device 22 across or otherwise into engagement with sensor 50.

The inlet door and outlet door then actuate to close (606). In this manner, no other fluid samples will engage sensor 50 and MAV then 10 flies to another location (608). In this scenario, MAV 10 may repeat the entire method as illustrated in FIG. 7, or MAV 10 may fly to any other remote location to report the quality characteristic of the sample.

Similar to the example illustrated in FIG. 5, sensor 50 may be configured to wirelessly transmit the quality characteristic of a fluid sample to a remote location. In one example, sensor 50 may perform a self-cleaning operation that enables MAV 10 to collect other quality characteristic(s) of fluid sample(s) during the same flight sequence. In this manner, MAV 10 may fly to multiple other locations to retrieve quality characteristic information from other fluid samples. MAV 10 may also fly to a location where the quality characteristic information of the fluid sample is physically or electronically retrieved from fluid sample device 22.

FIG. 8 is an elevation view of an example MAV 10 that is similar to FIG. 1. FIG. 8 includes all the same components of example MAV 10 of FIG. 1, including ducted fan 12, engine 14, pods 16 and 18, landing gear 20, and fluid sample device 22. Additionally, the example shown in FIG. 8 also includes flexible tube 40. Similar to FIG. 1, the example of FIG. 8 shows that engine 14 is located toward the inlet end of ducted fan 12 and mechanically connected (either directly or indirectly) to the ducted fan. As well, pods 16 and 18 are offset laterally and connected to central console 24 that includes engine 14 and handle 26. Furthermore, four landing gears 20 (only two are shown in the view of FIG. 1) are connected to ducted fan 12. The only difference between FIG. 1 and FIG. 8 is flexible tube 40, which is attached to an outer surface of pod 18. The illustration of FIG. 8 is intended to show how to detect quality characteristics of materials collected from the ground over which MAV 10 flies.

Flexible tube 40 is attached to an outer surface of pod 18 and connected to an inlet of fluid sample device 22. Flexible tube 40 is configured such that the working fluid drawn by the rotor fan through duct 28 generates a pressure differential that causes a sample to be drawn from a distal end of the tube into the fluid sampling device through the inlet to engage sensor 50 and then be drawn out of the outlet of the device. Flexible tube 40 extends in a distal direction from fluid sample device 22. When MAV 10 hovers over a target location, the distal end of flexible tube 40 may be located near landing gears 20.

In one example, when MAV 10 flies adjacent to the ground, the working fluid flow that is drawn by the rotor fan through the duct and exits the duct agitates materials located on the ground, including solid particulate material like dust and liquids like pools of water or other liquids. In this manner, operation of MAV 10 above the ground propels material and moisture from the ground into the air. The materials are drawn into the distal end of flexible tube 40 toward fluid sample device 22, which is thereby able to collect ground material and atomized moisture that are airborne near the MAV. The ground material and moisture may be drawn through the distal end of the flexible tube and directed up in to the inlet of fluid sample device 22 to engage sensor 50 arranged within fluid sample device 22.

In another example, the pressure differential generated by the rotor fan of ducted fan 12 of MAV 10 is powerful enough that flexible tube 40 is able engage, or suck, material and moisture directly from the ground. In this manner, there may be no need for the working fluid flow drawn by the rotor fan through duct 28 to agitate the ground material and atomize the moisture.

Figure 8:
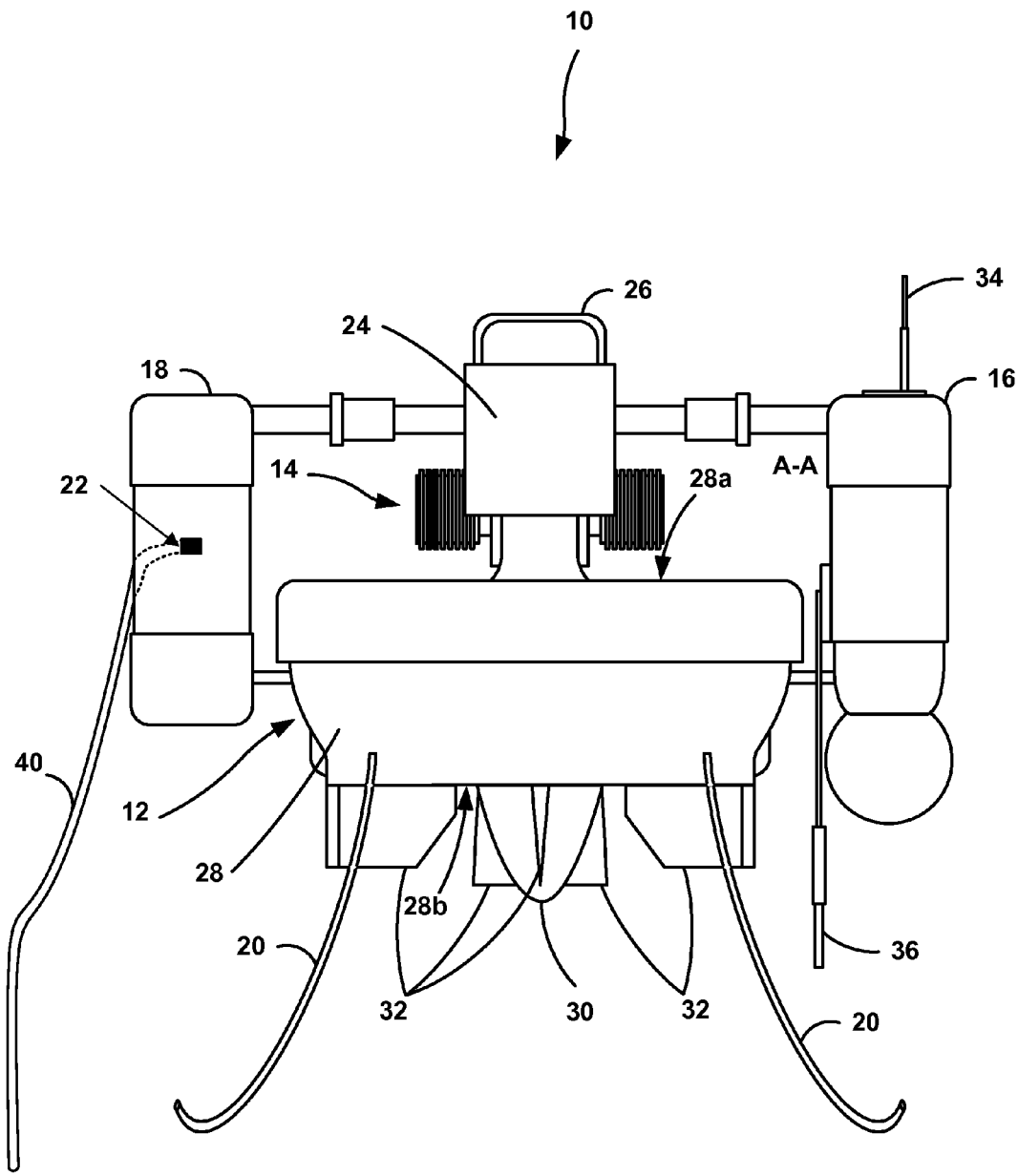
FIG. 8 is an elevation view of another example MAV according to this disclosure.

In the example of FIG. 8 flexible tube 40 is rubber. In another example, flexible tube 40 is plastic. However, flexible tube 40 may be constructed of any material that is able to be easily cleaned and robust enough for multiple uses. In this manner, when MAV 10 may be piloted to a different location away from where it engaged the material and/or moisture sample, the inside and/or outside of flexible tube may be swabbed to determine whether the tube contains any residue of material or moisture, which can then be tested for quality characteristics as well.

In regards to the size of flexible tube 40, the length of flexible tube 40 may be dependent upon the size of the MAV and the distance over the ground the MAV 10 must operate in order to effectively collect samples. In an example similar to that shown in FIG. 8, the distal end of flexible tube 40 may extend to less than approximately three inches above the distal end of landing gears 20, when landing gears 20 are deployed for landing. In another example, the distal end of flexible tube may extend less or more away from the distal end of deployed landing gears 20. For example, the distal end of flexible tube 40 may extend to just below the outlet of duct 28. The inner diameter of flexible tube 40 may be relatively small, in comparison to the overall size of MAV 10. In one example, the inner diameter is less than one inch. In another example, the inner diameter is one-eighth inch. In other examples, the inner diameter of flexible tube 40 may be any distance between one-eighth inch and one-half inch.

Figure 9:
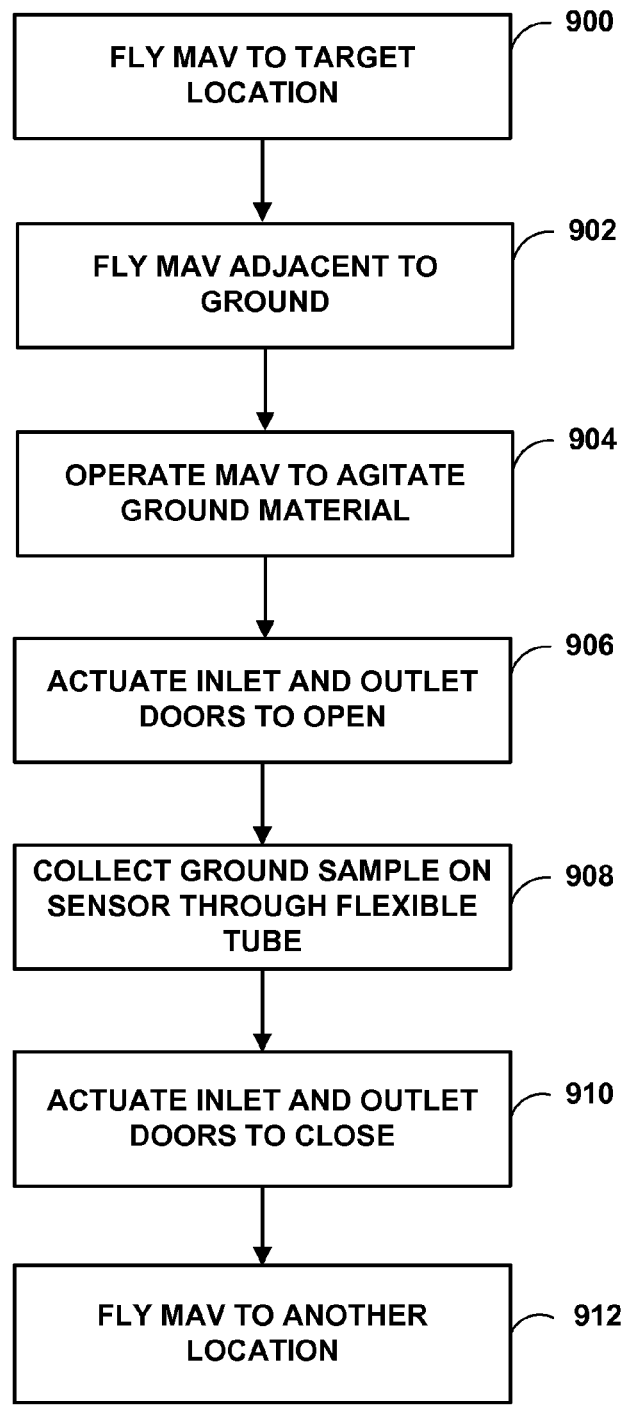
FIG. 9 is a flow chart illustrating a method of detecting a quality characteristic of a ground material and/or ground moisture using a MAV.

FIG. 9 is a flow chart illustrating a method of detecting a quality characteristic of a ground material using MAV 10. The method illustrated in FIG. 9 is similar to the method illustrated in FIG. 7; however, FIG. 9 further includes steps to collect materials from the ground over which MAV 10 flies using flexible tube 40, as described above. Like FIGS. 5 and 6, the functions of the method of FIG. 9 for detecting a quality characteristic of a ground material are described as carried out by the various components as shown by the examples in FIGS. 1-8.

In the method of FIG. 9, MAV 10 flies to a target location (900). The target location may be a programmed instruction that is stored in memory 48 at the time that MAV initiates its flight sequence. The target location may also be transmitted to MAV 10 via a wireless communication that is received by avionics 44. The target location may also be a location that MAV 10 determines via processor 58.

MAV 10 then flies adjacent to the ground (902) and MAV 10 operates in such a way that materials on the ground are agitated (904). MAV 10 may agitate the ground materials by performing an in-flight maneuver such as hovering adjacent to the ground. This hovering maneuver may be performed at any appropriate distance from the ground. In one example, MAV 10 flies within three to ten feet of the ground to agitate materials and moisture. In another example MAV 10 flies within less than three feet of the ground to agitate materials and moisture. In yet another example, MAV 10 makes contact with the ground via landing gears 20 to agitate materials and moisture.

In addition to flying adjacent to the ground (902), the method of FIG. 9 includes the inlet door and outlet door being actuated to open (906). Inlet door 54 and outlet door 56 may be actuated to open to varying degrees, in other words, the size of the opening formed by the inlet and outlet doors may vary. In such a case, inlet door 54 and outlet door 56 may be configured to control the fluid flow rate and pressure that flows through fluid sample device 22. In another example, inlet door 54 and outlet door 56 are actuated to completely open. Additionally, inlet door 54 and outlet door 56 may be actuated to open, whether to the same or varying degrees, independent of one another.

As MAV 10 agitates ground material and moisture, the agitation propels ground material and moisture airborne. The sensor contained within the fluid sample device then collects the airborne ground material and/or moisture sample via the pressure differential that flows from the distal end of a flexible tube toward the fluid sample device (908). The pressure differential is caused by the fluid flow that is drawn by the rotor fan through the duct, which effectively sucks airborne ground material and/or moisture into the distal end of flexible tube 40 into the inlet of fluid sample device 22 where it engages sensor 50.

Once sensor 50 has engaged ground material and/or moisture, inlet door 54 and outlet door 56 are then actuated to close (910). MAV 10 may then fly to another location (912) where MAV 10 may repeat the entire method illustrated in FIG. 9. In another example, MAV 10 may fly to any other remote location where it may report the quality characteristics of the ground material and/or moisture sample.

Sensor 50 may be configured to wirelessly transmit the quality characteristic(s) of the collected ground material and/or moisture to a remote location. In one example, sensor 50 may perform a self-cleaning operation that enables MAV 10 to collect other quality characteristic(s) of ground material and/or moisture during the same flight sequence. In this manner, MAV 10 may fly to multiple other locations to retrieve quality characteristic information from other samples. MAV 10 may also fly to a location where the quality characteristic information of ground samples is physically or electronically retrieved from fluid sample device 22.

Various examples have been described. These and other examples are within the scope of the following claims.

The invention claimed is:
1. A ducted fan for a vertical take-off and landing (VTOL) vehicle, the ducted fan comprising:
  a rotor fan;
  an engine operatively connected to and configured to cause rotation of the rotor fan;

an annular duct surrounding the fan, wherein rotation of the rotor fan causes a working fluid to be drawn through the duct to generate thrust to propel the VTOL;
an avionics pod attached to an outer section of the annular duct;
a fluid sample device attached to the avionics pod,
wherein the fluid sample device comprises a sensor configured to detect a quality characteristic of a fluid that engages the sensor, and
wherein the fluid sample device is arranged such that a working fluid drawn by the rotor fan through the duct engages the sensor.

2. The ducted fan of claim 1, wherein the fluid sample device comprises an inlet door on a first side of the fluid sample device and an outlet door on a second side of the fluid sample device opposing the first side, and wherein the inlet door and outlet door are configured to be adjusted to control a fluid flow to an interior section of the fluid sample device.

3. The ducted fan of claim 2, wherein the inlet door and outlet door are configured to be actuated autonomously.

4. The ducted fan of claim 2, wherein the inlet door and outlet door are both actuated by a motor that is located within the interior section of the fluid sample device.

5. The ducted fan of claim 4, further comprising avionics that are contained within the avionics pod, wherein the avionics comprise a digital processor, and wherein the digital processor is configured to control the motor and to receive a signal from the sensor indicative of the quality characteristic of the fluid sample.

6. The ducted fan of claim 1, wherein the sensor is selected from the group consisting of a chemical, biological, radiological, nuclear, and explosive sensor.

7. The ducted fan of claim 1, wherein the sensor comprises a collection membrane.

8. The ducted fan of claim 7, wherein the collection membrane is chemically coated, and wherein the chemical coating is configured to generate a visible indication based on the quality characteristic detected by the collection membrane.

9. The ducted fan of claim 7, wherein the collection membrane is a cassette that is configured to be removable.

10. The ducted fan of claim 9, wherein the cassette is attached to the fluid sample device with a hook-and-loop fastening system.

11. The ducted fan of claim 1, further comprising a flexible tube configured to be attached to an outer surface of the avionics pod, wherein the tube is connected to an inlet of the fluid sampling device and configured such that the working fluid drawn by the rotor fan through the duct generates a pressure differential that causes a fluid to be drawn from a distal end of the tube into the fluid sampling device through the inlet and engage the sensor.

12. The ducted fan of claim 11, wherein the tube is rubber or plastic.

13. The ducted fan of claim 1, wherein the avionics pod comprises a battery and avionics, and wherein the fluid sampling device is arranged between the battery and the avionics.

14. The ducted fan of claim 1, further comprising a radio transceiver, and wherein the fluid sample device is configured to analyze the quality characteristic and wirelessly communicate results of the analysis to a remote computing device via the radio transceiver.

15. The ducted fan of claim 1, wherein the quality characteristic comprises at least one of sulphur dioxide, any oxide of nitrogen, ozone, carbon monoxide, carbon dioxide, hydrogen sulphide, non-methane hydrocarbon, benzene, toluene, xylene, lead, ammonia, methane, solar radiation, suspended particulate matter, or any respirable particulate matter.

16. A method comprising:
flying a vertical take-off and landing (VTOL) vehicle to a location, wherein the VTOL comprises a rotor fan, an engine operatively connected to and configured to cause rotation of the rotor fan, an annular duct surrounding the fan, and an avionics pod attached to an outer section of the annular duct, wherein the rotation of the rotor fan causes a working fluid to be drawn through the duct to generate thrust to propel the VTOL;
collecting a sample of working fluid on a fluid sample device that is attached to the avionics pod, wherein the fluid sample device comprises a sensor that is configured to detect a quality characteristic of the fluid that engages the sensor, and wherein the fluid sample device is arranged such that the working fluid drawn by the rotor fan through the duct engages the sensor; and
flying the VTOL vehicle to another location.

17. The method of claim 16, further comprising actuating an inlet door that is operatively connected to the VTOL vehicle so that the inlet door opens; actuating an outlet door that is operatively connected to the VTOL vehicle so that the outlet door opens; actuating the inlet door so that the inlet door closes; and actuating the outlet door so that the outlet door closes.

18. The method of claim 16, wherein the sensor is configured to analyze the quality characteristic and wirelessly communicate the results.

19. The method of claim 16, further comprising flying the VTOL vehicle adjacent the ground; operating the VTOL vehicle such that the working fluid flowing through the duct agitates a ground material; and collecting a sample of the ground material on the sensor through a flexible tube attached to an outer surface of the avionics pod, wherein the tube is connected to an inlet of the fluid sampling device and configured such that the working fluid drawn by the rotor fan through the duct generates a pressure differential that causes the ground material to be drawn from a distal end of the tube into the fluid sampling device through the inlet and engage the sensor.

20. A method comprising:
flying a vertical take-off and landing (VTOL) vehicle to a location, wherein the VTOL comprises a rotor fan, an engine operatively connected to and configured to cause rotation of the rotor fan, an annular duct surrounding the fan, an avionics pod attached to an outer section of the annular duct, and a fluid sample device that is attached to the avionics pod, wherein the rotation of the rotor fan causes a working fluid to be drawn through the duct to generate thrust to propel the VTOL, and wherein the fluid sample device comprises a sensor that is configured to detect a quality characteristic of a ground material that engages the sensor;
flying the VTOL vehicle adjacent the ground;
operating the VTOL vehicle such that the working fluid flowing through the duct agitates the ground material;
collecting a sample of the ground material on the sensor through a flexible tube attached to an outer surface of the avionics pod, wherein the tube is connected to an inlet of the fluid sampling device and configured such that the working fluid drawn by the rotor fan through the duct generates a pressure differential that causes the ground material to be drawn from a distal end of the tube into the fluid sampling device through the inlet and engage the sensor; and
flying the VTOL vehicle to another location.

\* \* \* \* \*